US00PP26690P2

(12) United States Plant Patent
Pieters

(10) Patent No.: US PP26,690 P2
(45) Date of Patent: May 3, 2016

(54) ***CHRYSANTHEMUM* PLANT NAMED 'STAVISKI DARK RED'**

(50) Latin Name: *Chrysanthemum×morifolium*
Varietal Denomination: Staviski Dark Red

(71) Applicant: Dirk Pieters, Oostnieuwkerke (BE)

(72) Inventor: Dirk Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 0 days.

(21) Appl. No.: 14/121,541

(22) Filed: Sep. 17, 2014

(51) Int. Cl.
*A01H 5/02* (2006.01)

(52) U.S. Cl.
USPC ..... Plt./293

(58) Field of Classification Search
USPC ..... Plt./293
CPC ..... A01H 5/0255; A01H 5/025
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'Staviski Dark Red', characterized by its upright, outwardly spreading and rounded plant habit; moderately vigorous growth habit; freely branching habit; dense and full plant habit; uniform and freely flowering habit; small decorative-type inflorescences with dark red-colored ray florets; and excellent garden performance.

1 Drawing Sheet

Botanical designation: *Chrysanthemum×morifolium.*
Cultivar denomination: 'STAVISKI DARK RED'.

BACKGROUND OF THE INVENTION

The present invention relates to a new and distinct cultivar of *Chrysanthemum* plant, botanically known as *Chrysanthemum×morifolium,* and hereinafter referred to by the name 'Staviski Dark Red'.

The new *Chrysanthemum* plant is a product of a planned breeding program conducted by the Inventor in Oostnieuwkerke, Belgium. The objective of the breeding program is to create new freely flowering *Chrysanthemum* plants with unique and attractive ray floret coloration.

The new *Chrysanthemum* plant is a naturally-occurring whole plant mutation of *Chrysanthemum×morifolium* 'Staviski Red', not patented. The new *Chrysanthemum* plant was discovered and selected by the Inventor as a single flowering plant from within a population of plants of 'Staviski Red' in a controlled greenhouse environment in Oostnieuwkerke, Belgium in October, 2012.

Asexual reproduction of the new *Chrysanthemum* plant by vegetative cuttings was first conducted in a controlled greenhouse environment in Oostnieuwkerke, Belgium in January, 2013. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural conditions. The phenotype may vary somewhat with variations in environmental conditions such as temperature, daylength and light intensity, without, however, any variance in genotype.

The following traits have been repeatedly observed and are determined to be the unique characteristics of 'Staviski Dark Red'.

These characteristics in combination distinguish Staviski Dark Red' as a new and distinct *Chrysanthemum* plant:

1. Upright, outwardly spreading and rounded plant habit; moderately vigorous growth habit.
2. Freely branching habit; dense and full plant habit.
3. Uniform and freely flowering habit.
4. Small decorative-type inflorescences with dark red-colored ray florets.
5. Excellent garden performance.

Plants of the new *Chrysanthemum* differ primarily from the parent, 'Staviski Red', primarily in ray floret color as plants of new *Chrysanthemum* have darker and more intense red-colored ray florets than plants of 'Staviski Red'.

Plants of the new *Chrysanthemum* can also be compared to plants of *Chrysanthemum×morifolium* 'Foxy Marjorie Red', not patented. In side-by-side comparisons conducted in Oostnieuwkerke, Belgium, plants of the new *Chrysanthemum* differed from plants of 'Foxy Marjorie Red' in the following characteristics:

1. Plants of the new *Chrysanthemum* were larger and more vigorous than plants of 'Foxy Marjorie Red'.
2. Plants of the new *Chrysanthemum* had finer leaves than plants of 'Foxy Marjorie Red'.
3. With development, disc florets of plants of the new *Chrysanthemum* are more conspicuous than disc florets of plants of 'Foxy Marjorie Red'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type.

Colors in the photograph may differ slightly from the color values cited in the detailed botanical description which accurately describe the colors of the new *Chrysanthemum* plant.

The photograph comprises a side perspective view of a typical flowering plant of 'Staviski Dark Red' grown in a container.

DETAILED BOTANICAL DESCRIPTION

The aforementioned photograph and following observations and measurements describe plants grown in 19-cm containers during the summer and autumn in an outdoor nursery in Oostnieuwkerke, Belgium and under cultural practices typical of commercial *Chrysanthemum* production. During the production of the plants, day temperatures ranged from 25° C. to 30° C. and night temperatures ranged from 15° C. to 20° C. Plants were grown under natural season conditions and were 20 weeks old when the photograph and detailed description were taken. In the following description, color references are made to The Royal Horticultural Society Colour Chart, 2005 Edition, except where general terms of ordinary dictionary significance are used.

Botanical classification: *Chrysanthemum×morifolium* 'Staviski Dark Red'.

Parentage: Naturally-occurring whole plant mutation of *Chrysanthemum×morifolium* 'Staviski Red', not patented.

Propagation:

*Type*.—Terminal vegetative cuttings.

*Time to initiate roots, summer*.—About 14 days at temperatures about 20° C.

*Time to initiate roots, winter: About* 20 days at temperatures about 20° C.

*Time to produce a rooted young plant, summer*.—About 30 days at temperatures about 20° C.

*Time to produce a rooted young plant, winter*.—About 40 days at temperatures about 20° C.

*Root description*.—Fine, fibrous; light brown in color.

*Rooting habit*.—Freely branching; medium density.

Plant description:

*Plant and growth habit*.—Perennial decorative-type *Chrysanthemum*; stems upright and outwardly spreading giving a uniformly rounded appearance to the plant; plants roughly spherical; very freely branching habit, about 25 primary lateral branches develop, each primary lateral branch with multiple secondary branches; pinching enhances lateral branch development; dense and full plant habit; moderately vigorous growth habit; plants flexible, not brittle.

*Plant height*.—About 45 cm.

*Plant width*.—About 60 cm.

*Lateral branches*.—Length: About 25 cm. Diameter: About 2 mm to 3 mm. Internode length: About 1 cm. Strength: Strong, flexible. Texture: Fine pubescent; longitudinally ridged. Color: Close to 144A.

*Leaves*.—Arrangement: Alternate, simple. Length: About 2 cm to 3.5 cm. Width: About 1.5 cm to 2 cm. Apex: Rounded to cuspidate. Base: Attenuate. Margin: Palmately lobed and serrate, sinuses between lateral lobes divergent to parallel. Texture, upper and lower surfaces: Slightly pubescent. Color: Developing leaves, upper surface: Close to 137C. Developing leaves, lower surface: Close to 137D. Fully expanded leaves, upper surface: Close to N137C; venation, close to 148C. Fully expanded leaves, lower surface: Close to 147B; venation, close to 147B to 147C. Petioles: Length: About 1 cm. Diameter: About 2 mm. Texture, upper and lower surfaces: Pubescent; slightly rough. Color, upper surface: Close to 146C. Color, lower surface: Close to 146D.

Inflorescence description:

*Appearance*.—Decorative inflorescence form; inflorescences borne on terminals above foliar plane; disc and ray florets arranged acropetally on a capitulum; inflorescences horizontal to peduncle axis.

*Fragrance*.—Slightly fragrant, pungent.

*Flowering response*.—Under natural season conditions, plants flower in late September in Belgium; flowering response time, about five weeks.

*Postproduction longevity*.—Inflorescences maintain good color and substance for about five weeks in an outdoor nursery; inflorescences persistent.

*Quantity of inflorescences*.—About 20 inflorescences develop per lateral branch.

*Inflorescence buds*.—Height: About 3 mm. Diameter: About 5 mm. Shape: Globular. Color: Close to 144A and 137C.

*Inflorescence diameter*.—About 3 cm.

*Inflorescence depth* (*height*).—About 1.5 cm.

*Disc diameter*.—About 7 mm.

*Receptacle diameter*.—About 3 mm.

*Receptacle height*.—About 2.5 mm to 3 mm.

*Receptacle color*.—Close to 144B.

*Ray florets*.—Length: About 5 mm to 10 mm. Width: About 3 mm. Shape: Oval. Apex: Rounded. Base: Attenuate. Margin: Entire. Aspect: Mostly flat. Texture, upper and lower surfaces: Smooth, glabrous. Number of ray florets per inflorescence: About 125 to 150 arranged in about five to six whorls. Color: When opening, upper surface: Close to 53A. When opening, lower surface: Close to 47A. Fully opened, upper surface: Close to 45A; color becoming closer to 53C with development. Fully opened, lower surface: Close to 47A; color becoming closer to 50B with development.

*Disc florets*.—Length: About 3 mm. Diameter: About 0.5 mm to 1 mm. Shape: Tubular; apices acute. Number of disc florets per inflorescence: About 100 to 150 massed at the center of the inflorescence. Color: Apex: Close to 144C. Mid-section: Close to 5B. Base: Close to 145D.

*Phyllaries*.—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles*.—Length, terminal peduncle: About 4 cm. Length, fourth peduncle: About 6 cm. Length, seventh peduncle: About 8 cm. Diameter: About 2 mm. Angle: About 30° from vertical. Strength: Moderately strong. Texture: Slightly pubescent. Color: Close to 146B.

*Reproductive organs*.—Androecium: Not observed. Gynoecium: Not observed.

*Seeds and fruits*.—Seed and fruit production have not been observed on plants of the new *Chrysanthemum*.

Disease & pest resistance: Resistance to pathogens and pests common to *Chrysanthemums* has not been observed on plants of the new *Chrysanthemum* grown under commercial conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Staviski Dark Red' as illustrated and described.

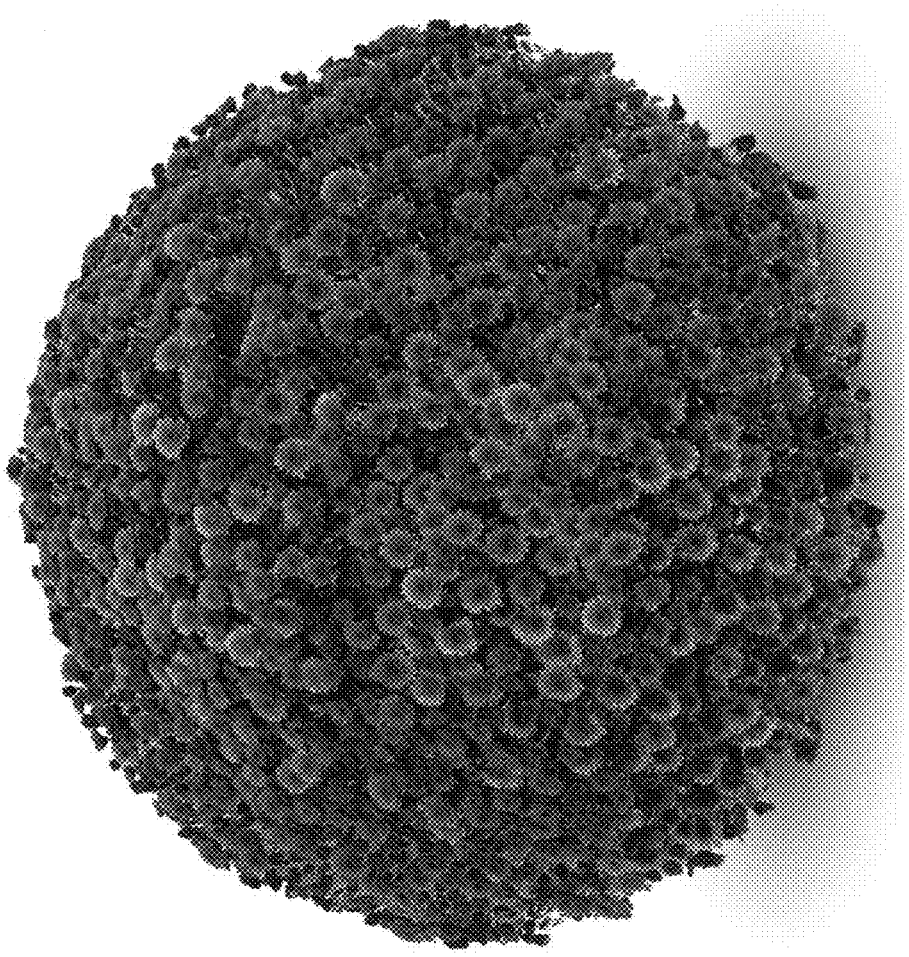

* * * * *